(12) United States Patent
Von Brunn

(10) Patent No.: US 8,522,777 B2
(45) Date of Patent: Sep. 3, 2013

(54) INHALER

(75) Inventor: Timo Von Brunn, Ingelheim (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 728 days.

(21) Appl. No.: 12/667,950

(22) PCT Filed: Jul. 4, 2008

(86) PCT No.: PCT/EP2008/005494
§ 371 (c)(1),
(2), (4) Date: Apr. 9, 2010

(87) PCT Pub. No.: WO2009/007069
PCT Pub. Date: Jan. 15, 2009

(65) Prior Publication Data
US 2010/0199986 A1    Aug. 12, 2010

(30) Foreign Application Priority Data

Jul. 6, 2007 (EP) ................................. 07013294

(51) Int. Cl.
*A61M 15/00* (2006.01)
*A61M 16/00* (2006.01)

(52) U.S. Cl.
USPC ............ 128/203.15; 128/203.12; 128/203.21; 128/203.23; 128/200.14

(58) Field of Classification Search
USPC ............ 128/203.12, 203.15, 203.21, 203.23, 128/204.26, 205.21; 222/80, 81
See application file for complete search history.

(56) References Cited

U.S. PATENT DOCUMENTS

2005/0005934 A1* 1/2005 Harvey .................... 128/203.15

FOREIGN PATENT DOCUMENTS

| CA | 2 297 174 A1 | 2/1999 |
|---|---|---|
| GB | 2 407 042 A | 4/2005 |
| WO | 94/12230 A1 | 6/1994 |
| WO | 99/07340 A1 | 2/1999 |
| WO | 2006/018261 A1 | 2/2006 |
| WO | 2006/079749 A2 | 8/2006 |
| WO | WO 2007068896 A1 * | 6/2007 |
| WO | 2007/096111 A2 | 8/2007 |

* cited by examiner

*Primary Examiner* — Clinton T Ostrup
(74) *Attorney, Agent, or Firm* — Roberts Mlotkowski Safran & Cole, P.C.; David S. Safran

(57) ABSTRACT

An inhaler for delivery of a powder-form inhalation formulation from a blister strip with a plurality of blister pockets. The used part of the blister strip with empty blister pockets is wound onto a drum which is driven via a gear mechanism which is coupled to the drum via a spring. The spring allows for the different peripheral speeds of the wound-up part to be compensated.

21 Claims, 1 Drawing Sheet

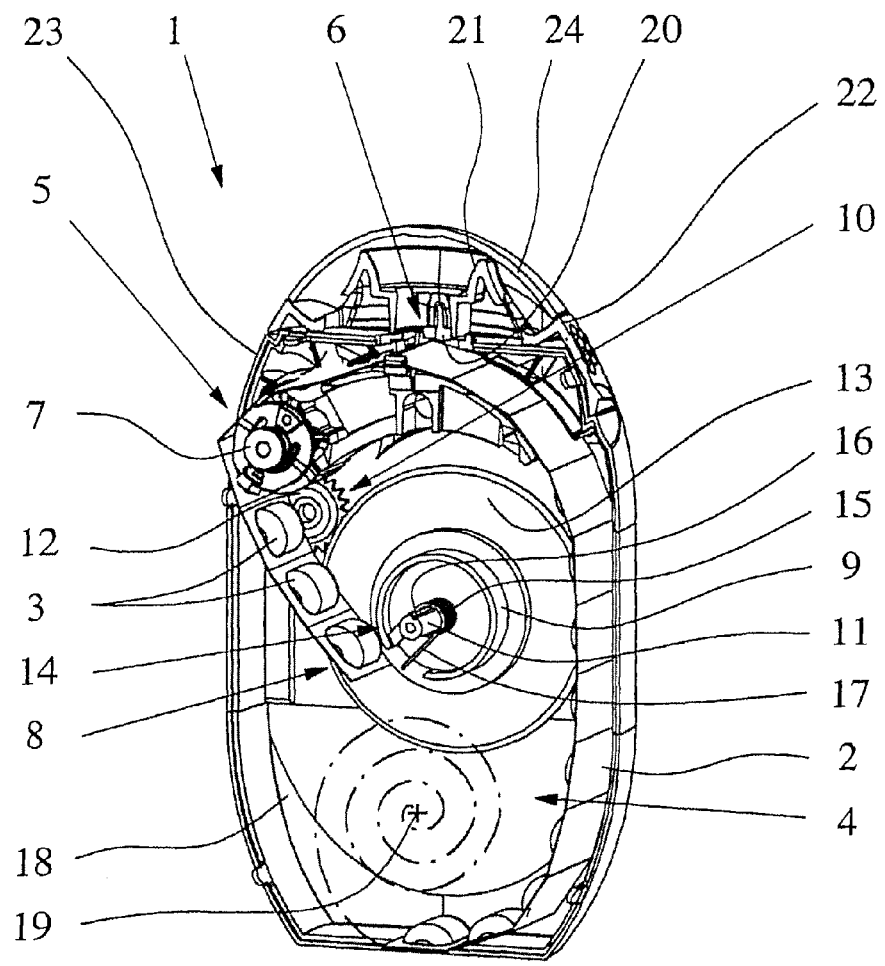

INHALER

BACKGROUND OF THE INVENTION

Field of Invention

The present invention relates to an inhaler for delivery of an inhalation formulation from a band-shaped blister strip with a plurality of blister pockets each of which contains one dose of the inhalation formulation.

The present invention relates to an inhaler for delivery of a powder-form inhalation formulation from a blister strip with a plurality of blister pockets (also called blisters) each of which contains a dose of the inhalation formulation. Usually the part of the blister strip with used (in particular opened and/or already empty) blister pockets—this part is also abbreviated to or called "used part" in the present invention—can be stored in the inhaler.

SUMMARY OF THE INVENTION

The object of the present invention is to provide an inhaler which makes possible an optimized storage of the used part of a band-shaped blister strip.

The above object is achieved by the provision of a conveyor for stepwise onward movement of the blister strip, and a receiving apparatus for receiving a used part of the blister strip, wherein the receiving apparatus comprises a drum onto which the used part is windable, wherein a transmission is provided for driving the drum, and wherein the transmission has a compensation element which has a variable transmission ratio.

The used part of the blister strip is wound onto a drum which is driven via a transmission, such as a gear mechanism, which is coupled with the drum via a compensation element, in particular a spring. This allows a compensation of different peripheral speeds of the wound-up part which occur due to the varying winding diameter. This allows a very simple and compact structure, wherein the used part of the blister strip is preferably always kept taut by the spring.

However, instead of the spring, another compensation element, variable in respect of the transmission ratio and/or not rigid, can also be provided in the transmission train of the receiving apparatus or its winder.

Further aspects, features, properties and advantages of the present invention will be apparent from the following description of a preferred embodiment, with reference to the accompany drawings.

BRIEF DESCRIPTION OF THE DRAWINGS

The sole FIGURE is a schematic representation an inhaler 1 in which the housing has been cut open.

DETAILED DESCRIPTION OF THE INVENTION

The inhaler 1 serves to deliver a preferably powder-form inhalation formulation from a band-shaped blister strip 2. The blister strip 2 is preferably finite, thus it does not form an endless or closed loop. It has a large number of blister pockets 3, each of which directly contains a dose of the preferably loose inhalation formulation. To inhale, and in particular upon inhalation, preferably, in each case, a dose of the inhalation formulation is removed from a blister pocket 3.

The inhaler 1 has a reservoir 4 for the still unused blister strip 2 with closed (sealed) blister pockets 3. In particular, the blister strip 3 is rolled up or wound up in the reservoir 4. In the embodiment represented, the reservoir 4 is formed such that the blister strip 2 can be moved outwards or pulled out of the reservoir as easily as possible.

In the embodiment represented, the blister strip 2 is directly received in the reservoir 4. However, instead of this, a cassette, a container, a drum or the like can also be fitted or inserted with the blister strip 2 into the inhaler 1 or the reservoir 4.

The inhaler 1 preferably has a conveyor 5 with a conveying wheel or any other suitable conveying means for the preferably stepwise onward movement of the blister strip 2, preferably by one blister pocket 3 each time, in order to feed the blister pockets 3 successively—i.e., one at a time—to an opening and/or removal position 6 for the opening and/or emptying of the respective blister pocket 3 one at a time—i.e., to allow access to and/or to remove the respective dose of the inhalation formulation.

In the embodiment represented, the conveying wheel 7, can engage between the blister pockets 3, and thus, convey the blister strip 2 in a preferably form-locking manner. The conveying apparatus 5 is preferably manually actuated.

The inhaler 1 comprises a piercing element 20 to puncture a lid of the respective blister pocket 3 in position 6, i.e., aligned with the piercing element 20. The piercing element 20 is hollow and in fluid connection with an adjacent mouthpiece 21 of the inhaler 1.

The inhaler 1 comprises a lever-like actuator 22 that is pivotally mounted to a housing 23 of the inhaler 1. The actuator 22 supports the piercing element 20 and mouthpiece 21.

The FIGURE shows the inhaler 1 with a mouthpiece cover 24 in the closed position. After opening the mouthpiece cover 24, the actuator 22 can be manually pivoted to retract the piercing element 20 from the last-pierced blister pocket 3 and to pierce the next one.

In the present embodiment, when the actuator 22 swivels from the shown position (in particular, about the axis of the conveying wheel 7 and here counterclockwise), the piercing element 20 is withdrawn from the last-pierced blister pocket 3. The swiveling of the actuator may move the blister strip 2 onwards. In particular, the blister strip 2 is thus conveyed onwards by one blister pocket 3.

When the actuator 22 swivels back into the shown position, the next blister pocket 3 of the blister strip 2 is pierced by the piercing element 20 and thereby opened. Thus, the inhaler 1 is ready again for the next inhalation.

During or for inhalation, a user places the mouthpiece 21 in his/her mouth and breathes in. The pierced and, thus, opened blister pocket 3, into which the piercing element 20 extends, is thereby emptied by being sucked-in. An air stream of ambient air is sucked in and passed through the opened blister pocket 3 such that the loose powder (not shown), preferably forming the inhalation formulation is delivered with the sucked-in ambient air as an aerosol cloud via the mouthpiece 21.

The inhaler 1 has a receiving apparatus 8 to receive or store the used part of the blister strip 2.

The receiving apparatus 8 is formed such that the used part can be wound up. The winding-up takes place onto a drum 9 of the receiving apparatus 8.

The inhaler 1 has a drive or transmission 10, in particular, a gear transmission, to wind up the used part, in particular, to drive the receiving apparatus 8 or the drum 9.

The drive or transmission 10 can drive the drum 9 either directly or indirectly according to choice.

In particular, the transmission 10 or a winding spindle or axle 11 of the transmission 10 houses or supports the drum 9.

Particularly preferably, the drum 9 concentrically surrounds the winding spindle or axle 11.

The receiving apparatus 8 preferably can be driven by the blister movement and/or conveyor 5. In particular, the winding-up is gear-coupled to the onward movement of the blister strip 2 via the transmission 10. Particularly preferably, the transmission 10 couples the conveyor 5 to the receiving apparatus 8 or vice versa.

In the representative embodiment, the conveying wheel 7 is coupled via an optional intermediate gear 12 to a winding wheel 13. In particular, the wheels 7, 12, 13 mesh and/or form a gear drive or gear transmission. In the representation according to FIGURE, the teeth of the wheels 7, 12, 13 are not clearly recognizable. In particular, a spur-gear unit is formed. However, any other suitable gear mechanism, for example, a traction transmission, in particular, a belt transmission or drive, can also be used.

The winding wheel 13 preferably forms or supports or is connected with the winding spindle or axle 11. However, here too, other design solutions are possible.

In the embodiment represented, the transmission 10 preferably has a fixed transmission ratio. In particular, the transmission ratio is chosen such that—at an average winding diameter or approximately at half the length of the part to be wound up in total—the peripheral speed of the used part driven by the transmission 10 would correspond substantially to the speed of the onward movement by the conveyor 5.

Alternatively, the transmission or gear mechanism 10 can also have a variable transmission ratio which is dependent, in particular, on the winding force, the winding length and/or the winding diameter.

The drive train for winding-up the used part or the transmission 10 has a compensation element 14 which is variable with respect to the transmission ratio and/or not rigid. This compensation element 14 serves, in particular, to compensate or keep constant the peripheral speed that otherwise (i.e., with constant anglular velocity) would vary with the winding diameter of the used part.

However, the compensation element 14 can also serve additional purposes.

In the embodiment represented, the compensation element 14 is associated with, and preferably connected to or integrated into, the transmission 10. In particular, the compensation element 14 couples the drum 9 to the transmission 10 or its winding spindle or axle 11, particularly preferably such that the drum 9 can be driven, but also—in particular, to only a certain extent—can be rotated relative to the winding spindle or axle 11.

The compensation element 14 is preferably a spring 15, in particular a leg or helical spring. In the embodiment represented, the spring 15 is, in particular, formed as a spiral spring with at least one leg, preferably two legs 16, 17.

In the embodiment represented, the spring 15 is arranged with its coils preferably concentric to the rotational axis or winding axle 11.

In the embodiment represented, the spring 15 can be coupled at one end to be fixed against rotation or is rotatable to only a limited extent relative to the winding axle 11, preferably via the leg 16, in particular, so that the winding axle 11 entrains or co-rotates the spring 15. Preferably, the leg 16 engages for this purpose in a corresponding recess, such as an axial groove.

The other end of the spring 15 or the other leg 17 of the spring 15 is coupled to the drum 9 in the embodiment represented. In particular, the leg 17 runs substantially radially and/or engages in a corresponding recess of the drum 9 and/or is fixed against rotation or is rotatable to only a limited extent relative to the drum 9. The drum 9 is preferably rotatably housed or supported on the winding axle 11. The provided rotary coupling of the drum 9 to the winding axle 11 or the drive train thus preferably takes place here via the spring 15.

In general, other design solutions are also possible. Furthermore, the compensation element 14 can alternatively or additionally also be formed as a freewheel, or other coupling.

In the embodiment represented, the transmission 10 forms, together with the compensation element 14, in particular, the spring 15, a gear train or a geared connection, with variable transmission, which depends in particular on the winding force or the winding diameter on the drum 9.

In the delivered or unused state of the inhaler 1, the blister strip 2 is preferably already guided through the conveyor 5 and connected at its free end to the drum 9. This ensures secure winding. However, here too other design solutions are possible, for example, such that the receiving apparatus 8 or drum 9 automatically grips the blister strip 2 or its free end and then winds up if the blister strip 2 is accordingly fed from the conveyor 5.

At the start of the winding-up process, the winding radius or diameter of the unused part on the drum 9 is minimal. Accordingly the peripheral speed, compared with the conveying speed of the conveyor 5, would be actually too low if the transmission 10 has constant angle velocity at its driving side and is designed such that—as is preferably the case—the peripheral speed with an average winding diameter at the angle velocity corresponds substantially to the conveying speed of the conveyor 5. This difference is compensated by the compensation element 14 or the spring 15. In fact, the spring 15 preferably is fitted in pretensioned stated so as to ensure that, at the start of the winding-up process, the drum 9 turns more in the winding-up direction than does the winding axle 11. Thus, the peripheral speed of the drum 9 then corresponds to the onward-movement speed of the conveyor 5.

In particular, the spring 15 ensures that the unused part of the blister strip 2 is always kept or guided taut in the inhaler 1. Particularly preferably, an undesired formation of loops or the like can thus be prevented. In the embodiment represented, the unused part of the blister strip 2 can thus be tensioned or drawn by the receiving apparatus 8.

During the first part of the winding-up process (relative to the overall length of the blister strip 2 to be wound up), the spring 15 is released until finally the winding diameter of the used part on the drum 9 is large enough for the angular speeds of the winding axle 11 and the drum 9 to briefly become equal. This can be the case, for example, approximately at half the length of the blister strip 2 to be wound up, at an average winding diameter or at any other point during the winding-up process and depends on the layout of the transmission 10, more precisely on the transmission ratio with which the winding axle 11 rotates relative to the conveying wheel 7 and on the drum diameter and the winding thickness of the blister strip 2.

In the course of the further winding-up, the spring 15 is then again increasingly tensioned. At the end of the winding-up process, the spring 15 can then be tensioned again, for example, as when delivered, or to a greater or lesser extent.

According to a modified embodiment, the transmission ratio of the transmission 10 can also be such that, for example, at the start, at the end or at any point during the winding-up process, the spring 15 is completely tensioned or released or is in its most or least tensioned state. Accordingly, the spring 15 can optionally also be fitted without pretensioning.

However, as already said, in principle, any suitable spring, such as a helical spring, spiral spring, clock spring or the like, can also be used. If necessary, the spring 15 can also be entirely dispensed with or be replaced or supplemented by another compensation element 14 that does not produce an (exclusively) rigid or fixed coupling or transmission or a flexible transmission element. As already mentioned, in particular, additionally or as an alternative to the spring 15, e.g., a ratchet mechanism, and/or a freewheel can be provided in the drive train.

As already mentioned, the compensation element 14 or the spring 15 compensates for different peripheral speeds of the wound-up part of the blister strip 2 which vary due to the varying winding diameter. However, a corresponding compensation can, for example, also or alternatively, be achieved by a sliding compensation, i.e., a clutch. In this case, the transmission ratio is, in particular, such that, with even the smallest winding diameter, the peripheral speed preferably already corresponds at least to the conveying speed of the conveyor 5. As the winding diameter increases, the sliding compensation then increasingly slips through.

In the embodiment represented, the spring 15 then leads to the used part of the blister strip 2 being pretensioned in winding-up direction, as already mentioned. The used part of the blister strip 2 is thus preferably always guided or kept taut and/or free of loops.

In the present embodiment, the unused part of the blister strip 2 (shown in wound-up form by dashed lines) and the receiving apparatus 8 for winding-up the used part preferably use a common housing space 18. In particular, the distance of the virtual axis 19 from the unused part of the winding axis or axle 11 is smaller than the sum of the maximum winding radius of the unused part and of the maximum winding radius of the used part. This allows a particularly good use of space, and accordingly, a particularly compact structure of the inhaler 1 similar as in video cassettes. However, in principle, a more distant arrangement of the two winding spaces is also possible.

The winding mechanism or the receiving apparatus 8 can be driven directly by the drive of the conveyor 5 via the transmission 10 as already described, or indirectly by the onward movement of the blister strip 2 via the transmission 10. Again, the compensation element 14, a freewheel or the like can be used for the possible compensation of any varying winding speeds or winding diameters.

The receiving apparatus 8 or winder can, if necessary, also form the conveyor 5 or replace it or vice versa. This simplifies the structure of the inhaler 1.

Particular advantages of the invention are that the blister strip 2 is wound up inside the inhaler 1, that there is a direct or geared transmission of the rotary movement or conveying movement to the receiving apparatus 8 or for winding including the compensation element 14, that the inhaler 1 is resistant to environmental influences, that the spring 15 is particularly preferably used as equalizing element or for compensation, and/or that the cost of assembly is only slightly increased as compared with inhalers 1 known from the state of the art.

The following substances or compounds are particularly preferably used as an inhalation formulation or effective constituent of the inhalation formulation.

The compounds named below can be used alone or in combination in the device according to the invention. In the compounds named below, W is a pharmacologically active ingredient and (for example) chosen from the group consisting of betamimetics, anticholinergics, corticosteroids, PDE4 inhibitors, LTD4 antagonists, EGFR inhibitors, dopamine agonists, H1 antihistamines, PAF antagonists and PI3 kinase inhibitors. Furthermore, double or triple combinations of W can be combined and be used in the device according to the invention. Combinations of W named by way of example would be:

W represents a betamimetic combined with an anticholinergic, corticosteroid, PDE4 inhibitor, EGFR inhibitor or LTD4 antagonist, W represents an anticholinergic combined with a betamimetic, corticosteroid, PDE4 inhibitor, EGFR inhibitor or LTD4 antagonist, W represents a corticosteroid combined with a PDE4 inhibitor, EGFR inhibitor or LTD4 antagonist W represents a PDE4 inhibitor combined with an EGFR inhibitor or LTD4 antagonist W represents an EGFR inhibitor combined with an LTD4 antagonist Preferably used here as betamimetics are compounds which are chosen from the group consisting of albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinoline-2-one 4-hydroxy-7-[2-{[2-{[3-(2-phenylethoxy)propyl]sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino]ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(4-phenoxy-ethyl acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1,1-dimethyl-ethylamino]ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert.-butylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)-phenyl]-formamide 8-hydroxy-5-(1-hydroxy-2-{2-[4-(6-methoxy-biphenyl-3-ylamino)-phenyl]-ethylamino}-ethyl)-1H-quinoline-2-one 8-hydroxy-5-[1-hydroxy-2-(6-phenethylamino-hexylamino)-ethyl]-1H-quinoline-2-one 5-[2-(2-{4-[4-(2-amino-2-methyl-propoxy)-phenylamino]-phenyl}-ethylamino)-1-hydroxy-ethyl]-8-hydroxy-1H-quinoline-2-one

[3-(4-{6-[2-hydroxy-2-(4-hydroxy-3-hydroxymethyl-phenyl)-ethylamino]-hexyloxy}-butyl)-5-methyl-phenyl]-urea 4-(2-{6-[2-(2,6-dichloro-benzyloxy)-ethoxy]-hexylamino}-1-hydroxy-ethyl)-2-hydroxymethyl-phenol 3-(4-{6-[2-hydroxy-2-(4-hydroxy-3-hydroxymethyl-phenyl)-ethylamino]-hexyloxy}-butyl)-benzylsulphonamide 3-(3-{7-[2-hydroxy-2-(4-hydroxy-3-hydroxymethyl-phenyl)-ethylamino]-heptyloxy}-propyl)-benzylsulphonamide 4-(2-{6-[4-(3-cyclopentanesulphonyl-phenyl)-butoxy]-hexylamino}-1-hydroxy-ethyl)-2-hydroxymethyl-phenol N-adamantane-2-yl-2-(3-{2-[2-hydroxy-2-(4-hydroxy-3-hydroxymethyl-phenyl)-ethylamino]-propyl}-phenyl)-acetamide optionally in the form of their racemates, enantiomers, diastereomers and optionally in the form of their pharmacologically acceptable acid addition salts, solvates or hydrates. Preferred according to the invention are the acid addition salts of betamimetics are chosen from the group consisting of hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

Preferably used here as anticholinergics are compounds which are chosen from the group consisting of tiotropium salts, preferably the bromide salt, oxitropium salts, preferably bromide salt, flutropium salts, preferably the bromide salt, ipratropium salts, preferably the bromide salt, glycopyrronium salts, preferably the bromide salt, trospium salts, preferably the chloride salt, tolterodine. In the abovenamed salts, the cations represent the pharmacologically active constituents. The abovenamed salts preferably contain as anions chloride, bromide, iodide, sulphate, phosphate, methanesulphonate, nitrate, maleate, acetate, citrate, fumarate, tartrate, oxalate, succinate, benzoate or p-toluenesulphonate, wherein chloride, bromide, iodide, sulphate, methanesulphonate or p-toluenesulphonate are preferred as counterions. Of all the salts, the chlorides, bromides, iodides and methanesulphonates are particularly preferred.

Equally preferred anticholinergics are chosen from the salts of Formula AC-1

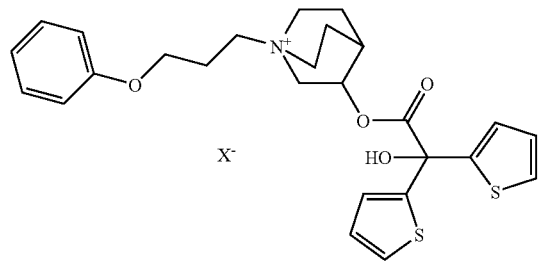

AC-1 in which $X^-$ represents a uninegative anion, preferably an anion chosen from the group consisting of fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably a uninegative anion, particularly preferably an anion chosen from the group consisting of fluoride, chloride, bromide, methanesulphonate and p-toluenesulphonate, particularly preferably bromide, optionally in the form of their racemates, enantiomers or hydrates. Of particular importance are medicinal product combinations which contain the enantiomers of Formula AC-1-en

AC-1-en in which $X^-$ can have the abovenamed meanings. Further preferred anticholinergics are chosen from the salts of Formula AC-2

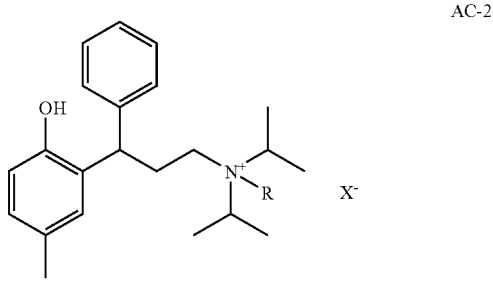

AC-2 in which R can represent either methyl or ethyl and in which $X^-$ can have the abovenamed meanings. In an alternative embodiment, the compound of Formula AC-2 can also be present in the form of the free base AC-2-base.

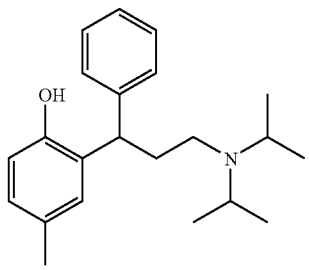

AC-2-base

Further named compounds are:
2,2-diphenylpropionic acid tropenol ester methobromide
2,2-diphenylpropionic acid scopine ester methobromide
2-fluoro-2,2-diphenylacetic acid scopine ester methobromide
2-fluoro-2,2-diphenylacetic acid tropenol ester methobromide
3,3',4,4'-tetrafluorobenzilic acid tropenol ester methobromide
3,3',4,4'-tetrafluorobenzilic acid scopine ester methobromide
4,4'-difluorobenzilic acid tropenol ester methobromide
4,4'-difluorobenzilic acid scopine ester methobromide
3,3'-difluorobenzilic acid tropenol ester methobromide
3,3'-difluorobenzilic acid scopine ester methobromide
9-hydroxy-fluorene-9-carboxylic acid tropenol ester methobromide
9-fluoro-fluorene-9-carboxylic acid tropenol ester methobromide
9-hydroxy-fluorene-9-carboxylic acid scopine ester methobromide
9-fluoro-fluorene-9-carboxylic acid scopine ester methobromide
9-methyl-fluorene-9-carboxylic acid tropenol ester methobromide
9-methyl-fluorene-9-carboxylic acid scopine ester methobromide
benzilic acid cyclopropyltropine ester methobromide
2,2-diphenylpropionic acid cyclopropyltropine ester methobromide
9-hydroxy-xanthene-9-carboxylic acid cyclopropyltropine ester methobromide
9-methyl-fluorene-9-carboxylic acid cyclopropyltropine ester methobromide
9-methyl-xanthene-9-carboxylic acid cyclopropyltropine ester methobromide
9-hydroxy-fluorene-9-carboxylic acid cyclopropyltropine ester methobromide
4,4'-difluorobenzilic acid methyl ester cyclopropyltropine ester methobromide
9-hydroxy-xanthene-9-carboxylic acid tropenol ester methobromide
9-hydroxy-xanthene-9-carboxylic acid scopine ester methobromide
9-methyl-xanthene-9-carboxylic acid tropenol ester methobromide
9-methyl-xanthene-9-carboxylic acid scopine ester methobromide
9-ethyl-xanthene-9-carboxylic acid tropenol ester methobromide
9-difluoromethyl-xanthene-9-carboxylic acid tropenol ester methobromide
9-hydroxymethyl-xanthene-9-carboxylic acid scopine ester methobromide The abovenamed compounds can also be used within the framework of the present invention as salts in which instead of the methobromide the metho-X salts are used, wherein X can have the meanings named above for $X^-$.

Preferably used here as corticosteroids are compounds which are chosen from the group consisting of beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
6,9-difluoro-17-[(2-furanylcarbonyl)oxy]-11-hydroxy-16-methyl-3-oxo-androsta-1,4-dien-17-carbothionic acid (S)-fluoromethyl ester
6,9-difluoro-11-hydroxy-16-methyl-3-oxo-17-propionyloxy-androsta-1,4-dien-17-carbothionic acid (S)-(2-oxo-tetrahydro-furan-3S-yl)ester,
6α,9α-difluoro-11β-hydroxy-16α-methyl-3-oxo-17α-(2,2,3,3-tetramethylcyclopropylcarbonyl)oxy-androsta-1,4-dien-17β-carboxylic acid cyanomethyl ester
optionally in the form of their racemates, enantiomers or diastereomers and optionally in the form of their salts and derivatives, their solvates and/or hydrates. Every reference to steroids includes a reference to their possibly existing salts or derivatives, hydrates or solvates. Examples of possible salts and derivatives of steroids can be: alkali salts, such as for example sodium or potassium salts, sulphobenzoates, phosphates, isonicotinates, acetates, dichloroacetates, propionates, dihydrogen phosphates, palmitates, pivalates or also furoates.

Preferably used here as PDE4 inhibitors are compounds which are chosen from the group consisting of enprofylline, theophylline, roflumilast, ariflo (cilomilast), tofimilast, pumafentrine, lirimilast, arofylline, atizoram, D-4418, Bay-198004, BY343, CP-325,366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and
N-(3,5-dichloro-1-oxo-pyridine-4-yl)-4-difluoromethoxy-3-cyclopropylmethoxybenzamide
(−)p-[(4αR*,10bS*)-9-ethoxy-1,2,3,4,4a,10b-hexahydro-8-methoxy-2-methylbenzo[s][1,6]naphthyridine-6-yl]-N,N-diisopropylbenzamide
(R)-(+)-1-(4-bromobenzyl)-4-[(3-cyclopentyloxy)-4-methoxyphenyl]-2-pyrrolidone
3-(cyclopentyloxy-4-methoxyphenyl)-1-(4-N'-[N-2-cyano-5-methyl-isothioureido]benzyl)-2-pyrrolidone
cis[4-cyano-4-(3-cyclopentyloxy-4-methoxyphenyl)cyclohexane-1-carboxylic acid]
2-carbomethoxy-4-cyano-4-(3-cyclopropylmethoxy-4-difluoromethoxyphenyl)cyclohexane-1-one
cis[4-cyano-4-(3-cyclopropylmethoxy-4-difluoromethoxyphenyl)cyclohexane-1-oi]
(R)-(+)-ethyl[4-(3-cyclopentyloxy-4-methoxyphenyl)pyrrolidine-2-ylidene]acetate
(S)-(−)-ethyl[4-(3-cyclopentyloxy-4-methoxyphenyl)pyrrolidine-2-ylidene]acetate
9-cyclopentyl-5,6-dihydro-7-ethyl-3-(2-thienyl)-9H-pyrazolo[3,4-c]-1,2,4-triazolo[4,3-a]pyridine
9-cyclopentyl-5,6-dihydro-7-ethyl-3-(tert-butyl)-9H-pyrazolo[3,4-c]-1,2,4-triazolo[4,3-a]pyridine
optionally in the form of their racemates, enantiomers, diastereomers and optionally in the form of their pharmacologically acceptable acid addition salts, solvates or hydrates. Preferred according to the invention are the acid addition salts of betamimetics chosen from the group consisting of hydrochloride, hydrobromide, hydroiodide, hydrosuiphate, hydrophosphate, hydromethanesulphonate, hydrocitrate, hydromaleate, hydroacetate, hydrocitrate, hydrofumarate, hydrotartrate, hydrooxalate, hydrosuccinate, hydrobenzoate and hydro-p-toluenesulphonate.

Preferably used here as LTD4 antagonists are compounds which are chosen from the group consisting of montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1R)-3(3-(2-(2,3-dichlorothieno[3,2-b]pyridine-5-yl)-(E)-ethenyl)phenyl)-3 (2-(1-hydroxy-1-methylethyl)phenyl)propyl)thio)methyl) cyclopropane-acetic acid

[2-[[2-(4-tert-butyl-2-thiazolyl)-5-benzofuranyl]oxymethyl]phenyl]acetic acid optionally in the form of their racemates, enantiomers, diastereomers and optionally in the form of their pharmacologically acceptable acid addition salts, solvates or hydrates. Preferred according to the invention are the acid addition salts of betamimetics chosen from the group consisting of hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate. By salts or derivatives which the LTD4 antagonists may optionally be able to form are meant for example: alkali salts, such as for example sodium or potassium salts, alkaline-earth salts, sulphobenzoates, phosphates, isonicotinates, acetates, propionates, dihydrogen phosphates, palmitates, pivalates or also furoates.

Preferably used here as EGFR inhibitors are compounds which are chosen from the group consisting of cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]amino}-7-cyclopropylmethoxy-quinazoline 4-[(3-chloro-4-fluorophenyl)amino]-6-{[4-(N,N-diethylamino)-1-oxo-2-buten-1-yl]amino}-7-cyclopropyl-methoxy-quinazoline 4-[(3-chloro-4-fluorophenyl)amino]-6-{[4-(N,N-dimethylamino)-1-oxo-2-buten-1-yl]amino}-7-cyclopropyl-methoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-(R)-6-methyl-2-oxo-morpholin-4-yl)-1-oxo-2-buten-1-yl]amino}-7-cyclopropylmethoxy-quinazoline 4-[(3-chloro-4-fluoro-phenypamino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-(R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethypamino]-6-{[4-(N,N-bis-(2-methoxy-ethyl)-amino)}-oxo-2-buten-1-yl]amino)-7-cyclopropyl-methoxy-quinazoline 4-[(R)-(1-phenyl-ethyl)amino]-6-({[4-(N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino}1-oxo-2-buten-1-yl]amino}-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethinyl-phenyl)amino]-6,7-bis-(2-methoxy-ethoxy)-quinazoline 4-[(3-chloro-4-fluorophenyl)amino]-7-[3-(morpholin-4-yl)-propyloxy]-6-[(vinylcarbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenypamino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline 4-[(3-chloro-4-fluorophenyl)amino]-6-{[4-[N,N-bis-(2-methoxy-ethyl)-amino]-1-oxo-2-buten-1-yl}amino)-7-[(tetrahydrofuran-2-yl)methoxy]-quinazoline 4-[(3-ethinyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenypamino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidine-1-yl]-ethoxy}-7-methoxy-quinazoline 4-[(3-chloro-4-fluoro-phenyl)amino]-6-[1-(tert.-butyloxycarbonyl)-piperidine-4-yloxy]-7-methoxy-quinazoline 4-[(3-chloro-4-fluoro-phenypamino]-6-(trans-4-amino-cyclohexane-1-yloxy)-7-methoxy-quinazoline 4-[(3-chloro-4-fluoro-phenyl)amino]-6-(trans-4-methane-sulphonylamino-cyclohexane-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidine-4-yloxy)-7-methoxy-quinazoline 4-[(3-chloro-4-fluoro-phenyl)amino]-6-{1-[morpholin-4-yl)carbonyl]-piperidine-4-yloxy}-7-methoxy-quinazoline 4-[(3-chloro-4-fluoro-phenyl)amino]-6-{1-[methoxymethyl)carbonyl]-piperidine-4-yloxy}-7-methoxy-quinazoline 4-[(3-chloro-4-fluoro-phenyl)amino]-6-(piperidine-3-yloxy)-7-methoxy-quinazoline 4-[(3-chloro-4-fluoro-phenyl)amino]-6-[1-(2-acetylamino-ethyl)-piperidine-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexane-1-yloxy}-7-methoxy-quinazoline 4-[(3-chloro-4-fluoro-phenyl)amino]-6-{trans-4-[(morpholin-4-yl)carbonylamino]-cyclohexane-1-yloxy}-7-methoxy-quinazoline 4-[(3-chloro-4-fluoro-phenyl)amino]-6-{trans-4-[(morpholin-4-yl)sulphonylamino]-cyclohexane-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidine-1-yl)carbonyl]-piperidine-4-yloxy}-7-methoxy-quinazoline 4-[(3-chloro-4-fluoro-phenyl)amino]-6-(1-aminocarbonylmethyl-piperidine-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexane-1-yloxy)-7-methoxy-quinazoline 4-[(3-chloro-4-fluoro-phenyl)amino]-6-(cis-4-{N-[morpholin-4-yl)carbonyl]-N-methyl-amino}-cyclohexane-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexane-1-yloxy)-7-methoxy-quinazoline 4-[(3-chloro-4-fluoro-phenypamino]-6-(trans-4-ethane-sulphonylamino-cyclohexane-1-yloxy)-7-methoxy-quinazoline 4-[(3-chloro-4-fluoro-phenyl)amino]-6-(1-methanesulphonyl-piperidine-4-yloxy)-7-ethoxy-quinazoline 4-[(3-chloro-4-fluoro-phenyl)amino]-6-(1-methanesulphonyl-piperidine-4-yloxy)-7-(2-methoxy-ethoxy)-quinazoline 4-[(3-chloro-4-fluoro-phenyl)amino]-6-[1-(2-methoxy-acetyl)-piperidine-4-yloxy]-7-(2-methoxy-ethoxy)-quinazoline 4-[(3-chloro-4-fluoro-phenyl)amino]-6-(cis-4-acetylamino-cyclohexane-1-yloxy)-7-methoxy-quinazoline 4-[(3-ethinyl-phenyl)amino]-6-[1-(tert.-butyloxycarbonyl)-piperidine-4-yloxy]-7-methoxy-quinazoline 4-[(3-ethinyl-phenyl)amino]-6-(tetrahydropyran-4-yloxy)-7-methoxy-quinazoline 4-[(3-chloro-4-fluoro-phenyl)amino]-6-(cis-4-{N-[piperidine-1-yl)carbonyl]-N-methyl-amino}-cyclohexane-1-yloxy)-7-methoxy-quinazoline 4-[(3-chloro-4-fluoro-phenyl)amino]-6-(cis-4-{N-[(4-methyl-piperazine-1-yl)carbonyl]-N-methyl-amino}-cyclohexane-1-yloxy)-7-methoxy-quinazoline 4-[(3-chloro-4-fluoro-phenyl)amino]-6-{cis-4-[(morpholin-4-yl)carbonylamino]-cyclohexane-1-yloxy}-7-methoxy-quinazoline 4-[(3-chloro-4-fluoro-phenyl)amino]-6-{1-[2-(2-oxopyrrolidine-1-yl)ethyl]-piperidine-4-yloxy}-7-methoxy-quinazoline 4-[(3-chloro-4-fluoro-phenyl)amino]-6-{1-[(morpholin-4-yl)carbonyl]-piperidine-4-yloxy}-7-(2-methoxy-ethoxy)-quinazoline 4-[(3-ethinyl-phenyl)amino]-6-(1-acetyl-piperidine-4-yloxy)-7-methoxy-quinazoline 4-[(3-ethinyl-phenyl)amino]-6-(1-methyl-piperidine-4-yloxy)-7-methoxy-quinazoline 4-[(3-ethinyl-phenyl)amino]-6-(1-methanesulphonyl-piperidine-4-yloxy)-7-methoxy-quinazoline 4-[(3-chloro-4-fluoro-phenyl)amino]-6-(1-methyl-piperidine-4-yloxy)-7(2-methoxy-ethoxy)-quinazoline 4-[(3-chloro-4-fluoro-phenyl)amino]-6-(1-isopropyloxycarbonyl-piperidine-4-yloxy)-7-methoxy-quinazoline 4-[(3-chloro-4-fluoro-phenyl)amino]-6-(cis-4-methylamino-cyclohexane-1-yloxy)-7-methoxy-quinazoline 4-[(3-chloro-4-fluoro-phenyl)amino]-6-{cis-4-[N-(2-methoxy-acetyl)-N-methyl-amino]-cyclohexane-1-yloxy}-7-methoxy-quinazoline 4-[(3-ethinyl-phenyl)amino]-6-(piperidine-4-yloxy)-7-methoxy-quinazoline 4-[(3-ethinyl-phenyl)amino]-6-{1-(2-methoxy-acetyl)-piperidine-4-yloxy}-7-methoxy-quinazoline 4-[(3-ethinyl-phenyl)amino]-6-{1-[(morpholin-4-yl)carbonyl]-piperidine-4-yloxy}-7-methoxy-quinazoline 4-[(3-chloro-4-fluoro-phenyl)amino]-6-{1-[(cis-2,6-dimethyl-morpholin-4-yl)carbonyl]-piperidine-4-yloxy}-7-methoxy-quinazoline 4-[(3-chloro-4-fluoro-phenyl)amino]-6-{1-[(2-methyl-morpholin-4-yl)carbonyl]-piperidine-4-yloxy}-7-methoxy-quinazoline 4-[(3-chloro-4-fluoro-phenyl)amino]-6-{1-[(S,S)-(2-oxa-5-aza-bicyclo[2.2.1]hept-5-yl)carbonyl]-piperidine-4-yloxy}-7-methoxy-quinazoline 4-[(3-chloro-4-fluoro-phenyl)amino]-6-{1-[(N-methyl-N-2-methoxyethyl-amino)carbonyl]-piperidine-4-yloxy}-7-methoxy-quinazoline 4-[(3-chloro-4-fluoro-phenyl)amino]-6-(1-ethyl-piperidine-4-yloxy)-7-methoxy-quinazoline 4-[(3-chloro-4-fluoro-phenyl)amino]-6-{1-[(2-methoxy-ethyl)carbonyl]-piperidine-4-yloxy}-7-methoxy-quinazoline 4-[(3-chloro-4-fluoro-phenyl)amino]-6-{4-[(3-methoxypropyl-amino)-carbonyl]-piperidine-4-yloxy}-7-methoxy-quinazoline 4-[(3-chloro-4-fluoro-phenyl)amino]-6-[cis-4-(N-methanesulphonyl-N-methyl-amino)-cyclohexane-1-yloxy]-7-methoxy-quinazoline 4-[(3-chloro-4-fluoro-phenypamino]-6-[cis-4-(N-acetyl-N-methyl-amino)-cyclohexane]yloxy)-7-methoxy-quinazoline 4-[(3-chloro-4-fluoro-phenyl)amino]-6-(trans-4-methylamino-cyclohexane-1-yloxy)-7-methoxy-quinazoline 4-[(3-chloro-4-fluoro-phenyl)amino]-6-[trans-4-(N-methanesulphonyl-N-methyl-amino)-cyclohexane-1-yloxy]-7-methoxy-quinazoline 4-[(3-chloro-4-fluoro-phenyl)amino]-6-(trans-4-dimethylamino-cyclohexane-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexane-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidine-4-yloxy)-7-methoxy-quinazoline 4-[(3-chloro-4-fluoro-phenyl)amino]-6-(1-cyano-piperidine-4-yloxy)-7-methoxy-quinazoline optionally in the form of their racemates, enantiomers, diastereomers and optionally in the form of their pharmacologically acceptable acid addition salts, solvates or hydrates. Preferred according to the invention are the acid addition salts of betamimetics chosen from the group consisting of hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

Preferably used here as dopamine agonists are compounds which are chosen from the group consisting of bromocriptine, cabergoline, alpha-dihydroergocryptine, lisuride, pergolide, pramipexole, roxindole, ropinirole, talipexole, terguride and viozan, optionally in the form of their racemates, enantiomers, diastereomers and optionally in the form of their pharmacologically acceptable acid addition salts, solvates or hydrates. Preferred according to the invention are the acid addition salts of betamimetics chosen from the group consisting of hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

Preferably used here as H1 antihistamines are compounds which are chosen from the group consisting of epinastine, cetirizine, azelastine, fexofenadine, levocabastine, loratadine, mizolastine, ketotifen, emedastine, dimetindene, clemastine, bamipine, cexchloropheniramine, pheniramine, doxylamine, chlorophenoxamine, dimenhydrinate, diphenhydramine, promethazine, ebastine, desloratidine and meclozine, optionally in the form of their racemates, enantiomers, diastereomers and optionally in the form of their pharmacologically acceptable acid addition salts, solvates or hydrates. Preferred according to the invention are the acid addition salts of betamimetics chosen from the group consisting of hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

In addition, inhalable macromolecules can be used, as disclosed in EP 1 003 478 A1 or CA 2297174 A1.

The compound can also come from the group of derivatives of ergot alkaloids, triptanes, CGRP inhibitors, phosphodiesterase-V inhibitors, optionally in the form of their racemates, enantiomers, diastereomers and optionally in the form of their pharmacologically acceptable acid addition salts, solvates or hydrates.

As derivatives of ergot alkaloids: dihydroergotamine, ergotamine.

What is claimed is:

1. Inhaler for delivery of an inhalation formulation from a band-shaped blister strip with a plurality of blister pockets each of which contains one dose of the inhalation formulation, comprising:
   a piercing element to puncture a lid of the respective blister pocket,
   a conveyor for stepwise onward movement of the blister strip, and
   a receiving apparatus for receiving an emptied blister strip,
   wherein the receiving apparatus comprises a drum onto which the emptied blister strip is windable,
   wherein a transmission is provided for driving the drum,
   wherein the transmission has a compensation element which has a variable transmission ratio, and
   wherein a manually swivellable actuator is provided that actuates both the piercing element and the receiving apparatus.

2. Inhaler according to claim 1, wherein the transmission is a gear mechanism.

3. Inhaler according to claim 1, wherein the transmission houses or supports the drum.

4. Inhaler according to claim 1, wherein the transmission drives the drum via the compensation element.

5. Inhaler according to claim 4, wherein the transmission has a winding axle which is rotatably coupled to the drum and wherein the drum concentrically surrounds the winding axle of the transmission.

6. Inhaler according to claim 1, wherein the compensation element is a spring that pre-tensions the used part of the blister strip in a winding direction.

7. Inhaler according to claim 1, wherein the transmission has a fixed transmission ratio, wherein the transmission ratio is set at an average winding diameter, or approximately half the total winding length, of the blister strip, so that a peripheral speed of the used part of the blister strip corresponds substantially to a speed of onward movement of produced by the conveyor.

8. Inhaler according to claim 1, wherein the transmission has a variable transmission ratio which is dependent on at least one of the winding force, the winding length and the winding diameter.

9. Inhaler according to claim 1, wherein the transmission couples the conveyor to the receiving apparatus.

10. Inhaler according to claim 1, wherein the receiving apparatus is drivable by the conveyor.

11. Inhaler according to claim 1, wherein winding-up is coupled to the onward movement of the blister strip.

12. Inhaler according to claim 1, wherein the conveyor has a rotatable conveying wheel for the stepwise onward movement of the blister strip, the conveying wheel being driven by a swivellable actuator.

13. Inhaler according to claim 12, wherein the transmission couples the conveying wheel to the receiving apparatus to wind up the used part.

14. Inhaler according to claim 1, wherein at least one of the conveyor, the piercing element and the receiving apparatus are actuatable by a manually swivellable actuator.

15. Inhaler according to claim 1, wherein the inhaler is activatable by breathing in during inhalation such that an air stream of ambient air can be sucked in to discharge the respective dose from an opened blister pocket and to deliver it with the ambient air as an aerosol cloud.

16. Inhaler according to claim 1, wherein an inhalation formulation in powder form is contained in each of the blister pockets in a quantity forming one dose of the inhalation formulation in loose form.

17. Inhaler according to claim 1, wherein the inhaler is of a size enabling it to be hand-held.

18. Inhaler according to claim 1, wherein the inhaler is adapted to be purely mechanically operated.

19. Inhaler according to claim 1, wherein the inhaler is only manually actuatable.

20. Inhaler for delivery of an inhalation formulation from a band shaped blister strip with a plurality of blister pockets each of which contains one dose of the inhalation formulation, comprising:

a conveyor for stepwise onward movement of the blister strip, and a receiving apparatus for receiving an emptied part of the blister strip, wherein the receiving apparatus comprises a drum onto which the emptied part of the blister strip is windable, wherein a transmission is provided for driving the drum, wherein the transmission has a compensation element which has a variable transmission ratio for ensuring that an unused part of the blister strip is kept taut despite a varying diameter of the emptied part of the blister strip, wherein the compensation element is a spring, wherein the spring is adapted for being released during a first part of a winding-up of the emptied part of the blister strip, and wherein the spring is adapted for being increasingly tensioned during a second part of the winding-up of the emptied part of the blister strip.

21. Inhaler for delivery of an inhalation formulation from a band shaped blister strip with a plurality of blister pockets each of which contains one dose of the inhalation formulation, comprising:

a conveyor for stepwise onward movement of the blister strip, and a receiving apparatus for receiving an emptied blister strip, wherein the receiving apparatus comprises a drum onto which the emptied blister strip is windable, wherein a transmission is provided for driving the drum, wherein the transmission has a compensation element which has a variable transmission ratio, wherein the unused blister strip and the receiving apparatus for winding-up the used blister strip use a common housing space, and wherein a distance between a virtual axis of the unused blister strip and a winding axis of the receiving apparatus is smaller than a sum of a maximum winding radius of the unused blister strip and a maximum winding radius of the used blister strip.

* * * * *